(12) United States Patent
Chern et al.

(10) Patent No.: US 10,598,587 B2
(45) Date of Patent: Mar. 24, 2020

(54) OPTICAL DEVICE

(71) Applicant: EVERREADY PRECISION IND. CORP., Kaohsiung (TW)

(72) Inventors: Jyh-Long Chern, Taipei (TW); Chih-Ming Yen, New Taipei (TW)

(73) Assignee: EVERREADY PRECISION IND. CORP., Kaohsiung (TW)

( * ) Notice: Subject to any disclaimer, the term of this patent is extended or adjusted under 35 U.S.C. 154(b) by 691 days.

(21) Appl. No.: 15/165,642

(22) Filed: May 26, 2016

(65) Prior Publication Data

US 2017/0184491 A1    Jun. 29, 2017

(30) Foreign Application Priority Data

Dec. 23, 2015   (TW) .............................. 104143363 A

(51) Int. Cl.
  *G01N 21/21*   (2006.01)
  *G01N 21/25*   (2006.01)
  (Continued)

(52) U.S. Cl.
  CPC ............ *G01N 21/21* (2013.01); *G01J 3/0232* (2013.01); *G01J 3/0256* (2013.01); *G01J 3/0272* (2013.01);
  (Continued)

(58) Field of Classification Search
  CPC ...... G01N 21/21; G01N 21/211; G01N 21/26; G01N 21/251; G01N 21/255; G01N 21/256; G01N 21/27; G01N 2021/213; G01N 2021/216; G01N 2021/4792; G01N 2021/4735; G01N 2021/4764; G01N 2021/4776; G01N 21/47; G01N 21/4738; G01N 21/474; G01N 21/49; G01N 2201/0221; G01N 2201/0222; G01J 1/0204; G01J 1/0233; G01J 1/0271; G01J 1/04; G01J 1/0403; G01J 1/044;
  (Continued)

(56) References Cited

U.S. PATENT DOCUMENTS 3,531,202 A * 9/1970 Spergel ..................... G01J 3/36
                                                            356/306
4,647,199 A * 3/1987 Ferber ....................... G01J 3/02
                                                            250/461.1
(Continued)

*Primary Examiner* — Gordon J Stock, Jr.
(74) *Attorney, Agent, or Firm* — Muncy, Geissler, Olds & Lowe, PC

(57) ABSTRACT

An optical device includes a door, a door control unit, a polarized light generation unit and a spectrum response analysis unit. The polarized light generation unit and the spectrum response analysis unit are located at a first side of the door. When the door is opened by the door control unit, a polarized light from the polarized light generation unit is transmitted through the door and externally projected on an under-test object at a second side of the door, so that a scattered light is generated. After the scattered light is returned back and transmitted through the door, the scattered light is projected on the spectrum response analysis unit, so that the spectrum response analysis unit performs a spectrum response analysis. The optical device has enhanced signal-to-noise ratio. Moreover, the optical device is capable of acquiring more explicit and diverse inherent information of the under-test object.

23 Claims, 6 Drawing Sheets

(51) Int. Cl.
  *G01N 21/47* (2006.01)
  *G01J 3/02* (2006.01)

(52) U.S. Cl.
  CPC .......... *G01N 21/255* (2013.01); *G01N 21/47* (2013.01); *G01N 2021/216* (2013.01); *G01N 2201/0221* (2013.01)

(58) Field of Classification Search
  CPC ....... G01J 2001/0257; G01J 2001/0261; G01J 3/02; G01J 3/0202; G01J 3/0232; G01J 3/0256; G01J 3/0272; G01J 3/0291; G01J 3/44; G01J 3/4412; G01J 3/447; G01J 4/02; G01J 4/04
  See application file for complete search history.

(56) References Cited

U.S. PATENT DOCUMENTS

| | | | | |
|---|---|---|---|---|
| 4,968,143 A * | 11/1990 | Weston | ...... | G01J 3/02 250/228 |
| 5,953,119 A * | 9/1999 | Zigler | ...... | G01J 3/02 356/318 |
| 7,535,569 B2 * | 5/2009 | De Vries | ...... | G01J 3/02 356/418 |
| 8,086,266 B2 * | 12/2011 | Kotidis | ...... | G01J 3/02 455/556.1 |
| 8,279,440 B2 * | 10/2012 | Frick | ...... | G01J 3/0202 356/402 |
| 8,345,226 B2 * | 1/2013 | Zhang | ...... | G01J 3/02 356/39 |
| 9,217,706 B2 * | 12/2015 | Mucci | ...... | G01N 21/3577 |
| 9,488,575 B2 * | 11/2016 | Kim | ...... | G01K 13/02 |
| 9,551,613 B2 * | 1/2017 | Majumdar | ...... | G01J 3/0221 |
| 9,581,496 B2 * | 2/2017 | Golub | ...... | H04N 5/23296 |
| 2006/0279732 A1 * | 12/2006 | Wang | ...... | G01J 3/02 356/326 |
| 2010/0309454 A1 * | 12/2010 | Zhang | ...... | G01J 3/02 356/39 |
| 2012/0206714 A1 * | 8/2012 | Higgins | ...... | G01J 3/0232 356/51 |
| 2013/0229646 A1 * | 9/2013 | Sakurai | ...... | G01J 3/45 356/51 |
| 2013/0270421 A1 * | 10/2013 | Kanamori | ...... | G02B 23/24 250/208.1 |
| 2014/0070076 A1 * | 3/2014 | Mallapragda | ...... | G01S 17/87 250/208.1 |
| 2014/0354868 A1 * | 12/2014 | Desmarais | ...... | H04N 5/23293 348/333.01 |
| 2015/0103334 A1 * | 4/2015 | Quant | ...... | G01N 21/718 356/51 |
| 2016/0103073 A1 * | 4/2016 | Ford | ...... | G01N 21/65 356/301 |
| 2016/0231171 A1 * | 8/2016 | Assefa | ...... | G01J 3/0272 |
| 2017/0131200 A1 * | 5/2017 | Raveh | ...... | G01N 21/21 |
| 2017/0135582 A1 * | 5/2017 | Cho | ...... | A61B 5/0075 |
| 2017/0292908 A1 * | 10/2017 | Wilk | ...... | G01J 3/0259 |
| 2017/0299515 A1 * | 10/2017 | Sasayama | ...... | G01N 21/645 |
| 2018/0080827 A1 * | 3/2018 | Kim | ...... | G01J 3/28 |

* cited by examiner

OPTICAL DEVICE

FIELD OF THE INVENTION

The present invention relates to an optical device, and more particularly to an optical device for spectrum detection and identification.

BACKGROUND OF THE INVENTION

With the development of electronic industries and the advance of industrial technologies, various electronic products are designed toward small size, light weightiness and easy portability. Consequently, these electronic products can be applied to mobile business, entertainment or leisure purposes whenever or wherever the users are. Recently, people pay much attention to the integrations and applications of mechanical, optical and electrical technologies. Consequently, a variety of optical devices such as image capturing devices or lighting devices are gradually and extensively applied to various electronic products (e.g., smart phones, wearable devices or other small-sized and portable electronic products). Consequently, according to the practical requirements, users can take the electronic products and use them whenever the users want. In other words, these electronic products not only have important commercial values but also provide more colorful lives to people.

With the improvement of the living quality, people's demands on more functions of the electronic products are gradually increased. Consequently, the demands on the optical devices of the electronic products are gradually increased. For meeting these demands, some micro spectrometers have been disclosed for acquiring the inherent information (e.g. ingredients, materials or properties) of an under-test object. For example, SCiO is a handheld molecular analyzer developed by Consumer Physics (an Israeli startup). The SCiO firstly projects a blue light onto the under-test object and then uses a near-infrared (NIR) technology to analyze the spectrum of the reflected light beams from the under-test object. Consequently, the ingredients of the under-test object (e.g., the calorie of food or the sugar content) or the plant growth conditions can be acquired.

In the related fields, other companies develop similar micro spectrometers. For example, the similar micro spectrometers include the Appllo sensor/nano spectrum-on-a-chip developed by Nano λ (nanolambda) of Korea, the micro spectrometer developed by Hamamatsu of Japan, and so on. Moreover, the micro spectrometer developed by Hamamatsu of Japan, e.g., C12666MA micro spectrometer, only has the element of receiving light beams but does not have the element of outputting light beams.

However, the conventional micro spectrometer has some drawbacks. For example, the signal-to-noise ratio (S/N ratio) is low, and the overall thickness fails to be effectively reduced. Since the pattern of the light beams projected on the under-test object is monotonous, the amount of inherent information obtained through the spectrum response analysis is limited. Therefore, the conventional technology needs to be further improved.

SUMMARY OF THE INVENTION

For solving the drawbacks of the conventional technologies, the present invention provides an optical device with enhanced signal-to-noise ratio (S/N ratio) and reduced overall thickness. Moreover, the optical device is capable of acquiring more explicit and diverse inherent information of the under-test object with specific projected light pattern in spatial domain, or temporal domain, and/or even spatial-temporal domain.

In accordance with an aspect of the present invention, there is provided an optical device. The optical device includes at least one door, a polarized light generation unit, a spectrum response analysis unit and a door control unit. The polarized light generation unit is located at a first side of the at least one door, and generates at least one polarized light. The spectrum response analysis unit is located at the first side of the at least one door. The door control unit is used for opening or closing the at least one door. When the at least one door is opened by the door control unit, the at least one polarized light is transmitted through the at least one door and externally projected on an under-test object at a second side of the at least one door, so that a scattered light is generated. After at least a portion of the scattered light from the under-test object is returned back and transmitted through the at least one door, the at least a portion of the scattered light is projected on the spectrum response analysis unit, so that the spectrum response analysis unit performs a spectrum response analysis on the at least a portion of the scattered light.

In an embodiment, the at least one polarized light includes at least one of a linearly polarized light, a circularly polarized light and an elliptically polarized light.

In an embodiment, the polarized light generation unit includes a light source.

In an embodiment, the light source is a polarized light source.

In an embodiment, the light source has a long-coherence-length property.

In an embodiment, the light source includes at least one of a laser diode, a light emitting diode, an organic light emitting diode and a thermal source.

In an embodiment, the polarized light generation unit further includes an optical element, and the optical element is arranged between the at least one door and the light source. When a source light from the light source is introduced into the optical element, the source light is split into the at least one polarized light by the optical element.

In an embodiment, after the at least a portion of the scattered light from the under-test object is returned back and transmitted through the at least one door, the at least a portion of the scattered light is guided to the spectrum response analysis unit by the optical element.

In an embodiment, the optical element includes a diffractive optical element.

In an embodiment, the diffractive optical element is a diffractive optical film.

In an embodiment, at least one of the wavelength-dependent coating and a polarization-dependent coating is formed on the optical element.

In an embodiment, the door is selectively opened or closed by the door control unit according to a time-sequence programming.

In an embodiment, the at least one door is a single door that is shared by the polarized light generation unit and the spectrum response analysis unit, or the at least one door comprises a first door corresponding to the polarized light generation unit and a second door corresponding to the spectrum response analysis unit.

In an embodiment, the first door and the second door are simultaneously opened or simultaneously closed.

In an embodiment, after the spectrum response analysis is performed, an inherent information of the under-test object is obtained.

In an embodiment, the inherent information contains an ingredient information, a material information, a texture information or a property information.

In an embodiment, the optical device is included in a portable electronic product.

In an embodiment, a thickness of the optical device is not larger than 7 mm.

In an embodiment, the optical device further includes a lens unit. The lens unit is arranged between the polarized light generation unit and the under-test object for collimating or focusing the at least one polarized light from the polarized light generation unit to the under-test object. Alternatively, the lens unit is arranged between the under-test object and the spectrum response analysis unit for collimating or focusing the at least a portion of the scattered light from the under-test object to the spectrum response analysis unit.

In an embodiment, the optical further comprises a reflective optical unit. The reflective optical unit is arranged between the polarized light generation unit and the under-test object for guiding a traveling direction of the at least one polarized light from the polarized light generation unit. Alternatively, the reflective optical unit is arranged between the under-test object and the spectrum response analysis unit for guiding a traveling direction of the at least a portion of the scattered light from the under-test object.

In an embodiment, the optical device further comprises a first lens unit and a second lens unit. The first lens unit is arranged between the polarized light generation unit and the under-test object. The second lens unit is arranged between the under-test object and the spectrum response analysis unit. The at least a portion of the scattered light is collected by the second lens unit. After the at least one polarized light from the polarized light generation unit passes through the first lens unit, a projected area of the at least one polarized light on the under-test object is adjusted.

In an embodiment, the polarized light generation unit is controlled by a time-varying programming such that the degree of polarization and intensity is varied.

In an embodiment, the at least one polarized light comprises a polarized structured light pattern with polarized property which is further detected by the spectrum response analysis unit which is a two-dimensional detection unit.

In an embodiment, the polarized structured light pattern is varied with time which can be programming by controlling the polarized light generation unit or the door control unit.

From the above descriptions, the door of the optical device of the present invention is selectively opened or closed. Consequently, the external light that is returned back from the under-test object can be received by the spectrum response analysis unit in a controllable time segment. That is, the spectrum response analysis unit is not continuously in the light-receiving state. Since the signal-to-noise ratio (S/N ratio) of the optical device is improved, the quality of the spectrum response analysis is enhanced. Moreover, after the polarized light is projected on the under-test object, the spectrum response is analyzed and thus the inherent information of the under-test object is detected. Moreover, according to the present invention, the pattern of the light projected on the under-test object is more diverse. For example, the light projected on the under-test object includes one of a linearly polarized light (e.g., an S-polarized light or a P-polarized light), a circularly polarized light and an elliptically polarized light. When a different pattern of the light is projected on the under-test object, a different spectrum response is produced. After the spectrum response analysis is completed, the optical device is capable of acquiring more explicit and diverse inherent information of the under-test object. Moreover, according to the structure design of the present invention, the overall thickness of the optical device is reduced. Especially, when the optical element of the optical device is designed as a film-type component, the overall thickness is further reduced.

The above objects and advantages of the present invention will become more readily apparent to those ordinarily skilled in the art after reviewing the following detailed description and accompanying drawings, in which:

DETAILED DESCRIPTION OF THE PREFERRED EMBODIMENT

Figure 1:
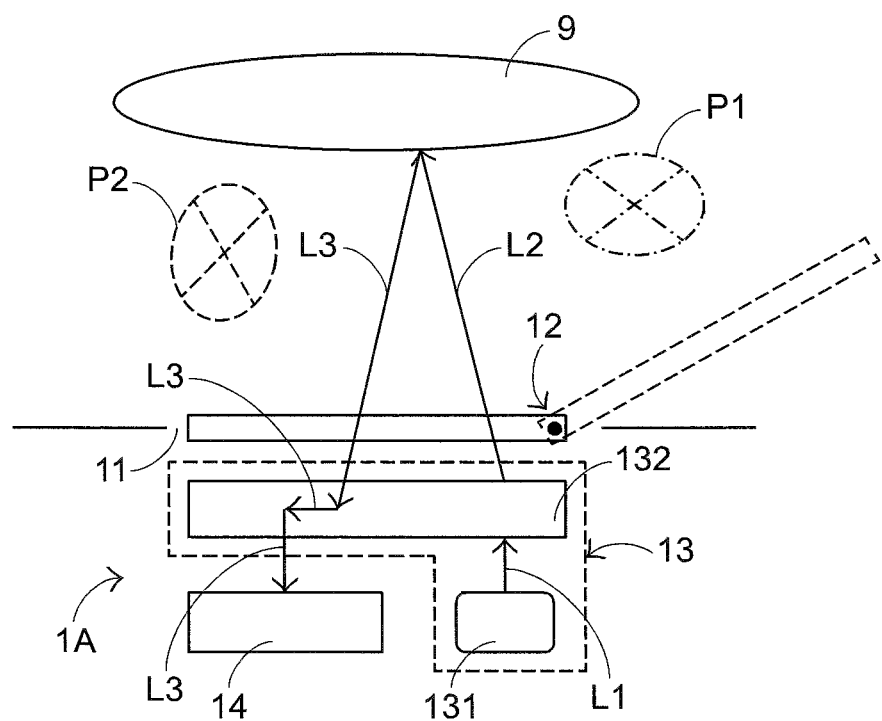
FIG. 1 schematically illustrates the operating concept of an optical device according to a first embodiment of the present invention.

FIG. 1 schematically illustrates the operating concept of an optical device according to a first embodiment of the present invention. As shown in FIG. 1, the optical device 1A comprises a door 11, a door control unit 12, a polarized light generation unit 13 and a spectrum response analysis unit 14. The door control unit 12 is in communication with the door 11. The polarized light generation unit 13 is located inside the door 11 and is controlled by a time-varying programming (not shown) such that the degree of polarization and intensity is varied. The spectrum response analysis unit 14 is also located inside the door 11. The polarized light generation unit 13 is used for generating a polarized light L2 w/o a polarized structured light pattern P1 with polarized property which is further detected by the spectrum response analysis unit 14 which is preferably a two-dimensional detection unit. Under control of the door control unit 12, the door 11 is selectively opened or closed.

In this embodiment, the polarized light generation unit 13 comprises a light source 131 and an optical element 132. The optical element 132 is arranged between the light source 131 and the door 11. The light source 131 emits a source light L1. When the source light L1 from the light source 131 is introduced into the optical element 132, the source light L1 is split into the polarized light L2 by the optical element 132. Moreover, when an external light L3 w/o a polarized structured light pattern P2 from the outside of the door 11 is introduced into the optical element 132, the external light L3 is guided to the spectrum response analysis unit 14 by the optical element 132. According to the pattern of the polarized light L2, the polarized light L2 includes at least one of a linearly polarized light (e.g., an S-polarized light or a P-polarized light), a circularly polarized light and an elliptically polarized light.

In an embodiment, the optical element 132 is a diffractive optical element (DOE). The optical element 132 is specially designed according to the practical requirements. Consequently, by means of the diffractive optical element, the source light L1 is split or the travelling direction of the external light L3 is guided. The ways of designing the diffractive optical element to output the lights L1 and L3 according to the user's requirements are well known to those skilled in the art, and are not redundantly described herein. Preferably but not exclusively, the diffractive optical element is a diffractive optical film. Consequently, the volume of the optical device 1A is further reduced. In some embodiments, a wavelength-dependent coating or a polarization-dependent coating is formed on the optical element 132 in order to modulate the lights L1 and L3. In an embodiment, the wavelength-dependent coating or the polarization-dependent coating is made of a material doped with fluorescent/phosphor powder. Alternatively, the wavelength-dependent coating or the polarization-dependent coating is made of a liquid crystal material, and is voltage-controlled or electrically controlled. Preferably but not exclusively, the overall thickness of the optical device 1A is not larger than 7 mm.

In an embodiment, the light source 131 includes a laser diode (LD), a light emitting diode (LED), an organic light emitting diode (OLED), a thermal source or any other comparable semiconductor-type light-emitting element similar to the laser diode, the light emitting diode or the organic light emitting diode. The wavelength of the source light L1 from the light source 131 is in a first wavelength range and/or a second wavelength range. For example, the source light L1 from the light source 131 is a visible light or an invisible light (e.g., an ultraviolet light, an infrared light, a near infrared light or a far infrared light).

The operations of the optical device 1A will be illustrated as follows. When the optical device 1A is used to detect an under-test object outside the door 11, the door 11 is opened under control of the door control unit 12. The opened door 11 as shown in FIG. 1 is indicated by dotted lines. Consequently, the polarized light L2 from the polarized light generation unit 13 is transmitted through the door 11 and externally projected on the under-test object 9. When the polarized light L2 is projected on the under-test object 9, the polarized light L2 is scattered by the under-test object 9. At least a portion of the scattered light from the under-test object 9 is the external light L3. The external light L3 is returned back and transmitted through the door 11. Then, the external light L3 is directly projected on the spectrum response analysis unit 14, or the external light L3 is guided to the spectrum response analysis unit 14 by the optical element 132. Meanwhile, the spectrum response analysis unit 14 performs a spectrum response analysis on the external light L3.

In case that the inherent information of the under-test object 9 is different, the under-test object 9 produces a different response to the polarized light L2. For example, when the polarized light L2 with the identical pattern is projected on a different under-test object 9, the under-test object 9 has a different absorption response, a different reflection response or any other different response to the polarized light L2 because the inherent information of the under-test object 9 is different. In case that the inherent information of the under-test object 9 is identical but the pattern of the polarized light L2 is different, the under-test object 9 produces a different response to the polarized light L2. Consequently, the inherent information of the under-test object 9 can be recognized according to the spectrum response analysis result of the spectrum response analysis unit 14.

Moreover, the door control unit 12 selectively opens or closes the door 11 according to a time-sequence programming. If the door 11 is opened or closed by the door control unit 12 according to the time-sequence programming, the polarized light L2 is projected on the under-test object 9 in a time-sequential manner. In some situations, the under-test object 9 produces a specified time-sequential response to the time-sequentially projected polarized light L2 on the under-test object 9 because of the specified inherent information of the under-test object 9. Consequently, when the polarized light L2 is projected on the under-test object 9 in the time-sequential manner, the inherent information of the under-test object 9 can be recognized according to the spectrum response analysis result of the spectrum response analysis unit 14.

Figure 6:
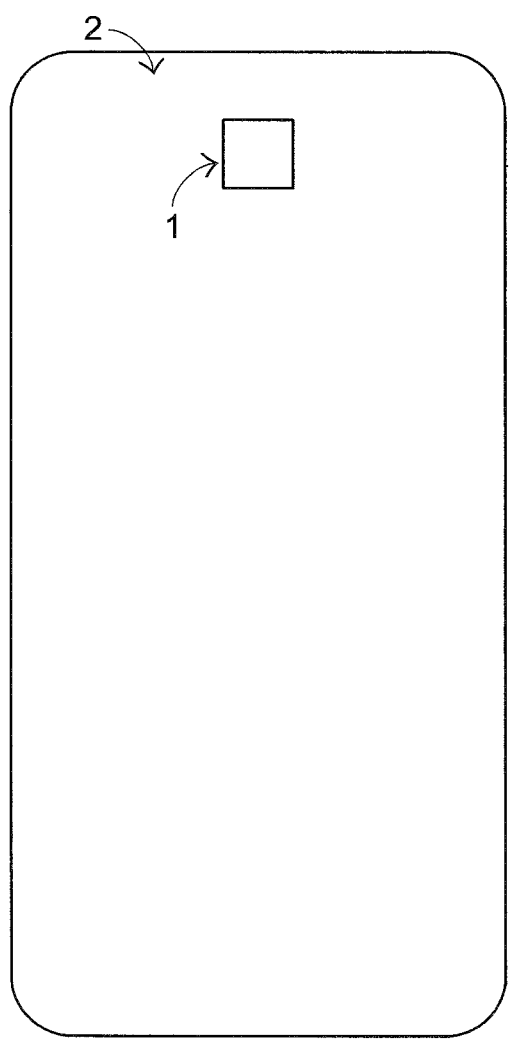
FIG. 6 schematically illustrates a portable electronic product using the optical device of the present invention.

Preferably but not exclusively, the recognizable inherent information contains the ingredient of the under-test object 9, the material or texture of the under-test object 9 and/or the property of the under-test object 9. Optionally, after the spectrum response analysis result is sent to a pre-built database (not shown) and compared with the stored data of the database, the inherent information of the under-test object 9 can be recognized. That is, the pre-built database contains various data of the inherent information and the corresponding spectrum response data to be compared with the spectrum response analysis result of the spectrum response analysis unit 14. Moreover, the pre-built database is stored in the optical device 1A, or the pre-built database is stored in an electronic product with the optical device 1A (e.g., a portable electronic product 2 as shown in FIG. 6), or the pre-built database is stored in a cloud storage device (not shown) through network connection.

Moreover, since the optical device 1A comprises the door 11 that is selectively opened or closed, the external light L3 that is returned back from the under-test object 9 can be received by the spectrum response analysis unit 14 in a controllable time segment. Under this circumstance, the spectrum response analysis unit 14 is only able to receive the external light L3 in a time interval between the generation and the terminal of the polarized light L2 from the polarized light generation unit 13. That is, the spectrum response analysis unit 14 is not continuously in the light-receiving state. Since the signal-to-noise ratio (S/N ratio) of the optical device 1A is improved, the quality of the spectrum response analysis is enhanced.

Figure 2:
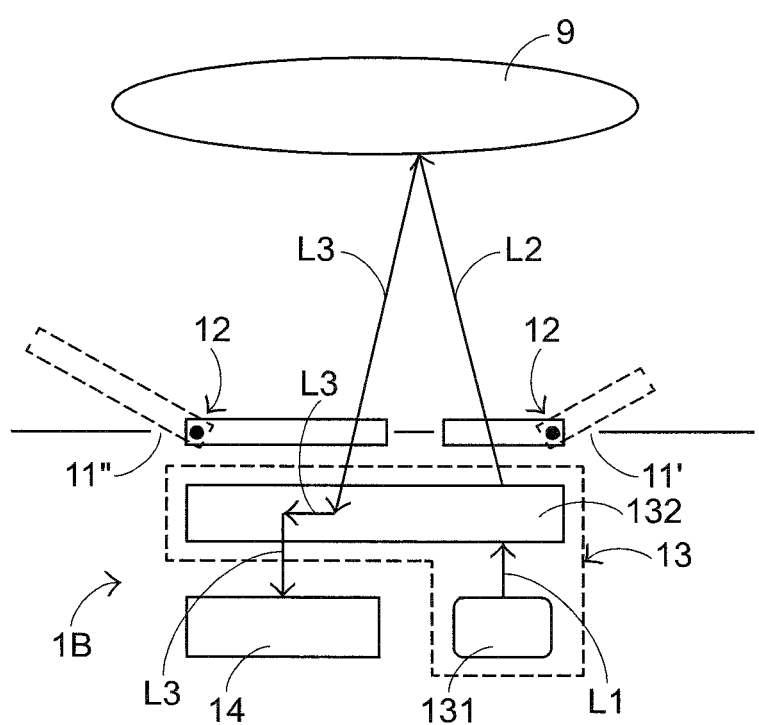
FIG. 2 schematically illustrates the operating concept of an optical device according to a second embodiment of the present invention.

FIG. 2 schematically illustrates the operating concept of an optical device according to a second embodiment of the present invention. The structure and function of the optical device 1B that are similar to those of the first embodiment are not redundantly described herein. In this embodiment, the polarized light generation unit 13 and the spectrum response analysis unit 14 of the optical device 1B do not have the shared door. That is, the optical device 1B comprises a first door 11' corresponding to the polarized light generation unit 13 and a second door 11" corresponding to the spectrum response analysis unit 14. When the first door 11' is opened, the polarized light L2 from the polarized light generation unit 13 is transmitted through the first door 11' and externally projected on the under-test object 9. When the second door 11" is opened, at least a portion of the scattered light from the under-test object 9 (i.e., the external light L3) is returned back and transmitted through the second door 11". Then, the external light L3 is directly projected on the spectrum response analysis unit 14, or the external light L3 is guided to the spectrum response analysis unit 14 by the optical element 132.

In case that the light source 131 of the polarized light generation unit 13 comprises a single light-emitting element, the first door 11' and the second door 11" are simultaneously opened and simultaneously closed. In case that the light source 131 of the polarized light generation unit 13 comprises plural light-emitting elements, the first door 11' and the second door 11" are simultaneously opened or simultaneously closed according to the practical requirements (e.g., according to the time sequence of providing the source light from each light-emitting unit).

Figure 3:
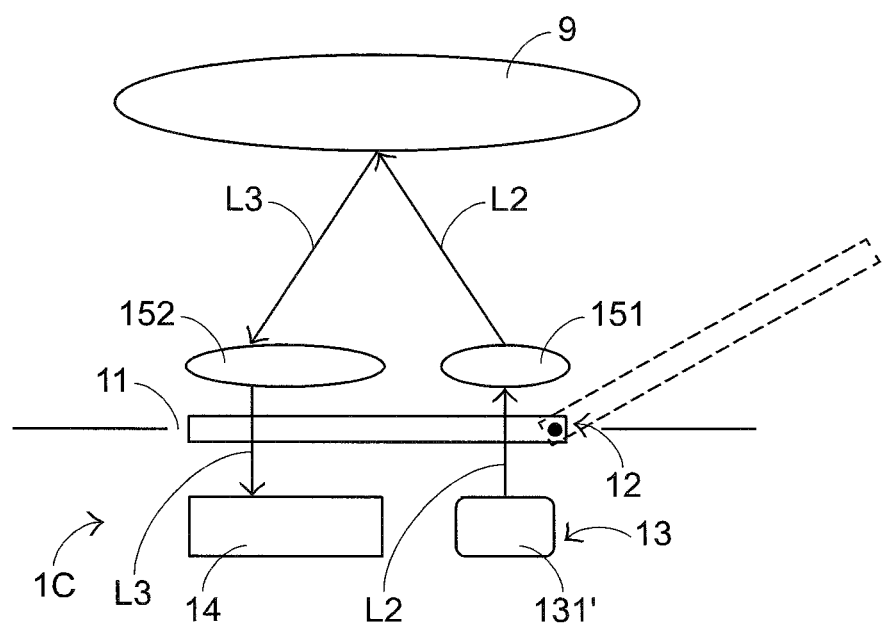
FIG. 3 schematically illustrates the operating concept of an optical device according to a third embodiment of the present invention.

FIG. 3 schematically illustrates the operating concept of an optical device according to a third embodiment of the present invention. The structure and function of the optical device 1C that are similar to those of the first embodiment are not redundantly described herein. In comparison with the first embodiment, the light source 131' of the polarized light generation unit 13' of the optical device 1C is a polarized light source for directly providing the polarized light L2. Under this circumstance, the optical device 1C is not equipped with the optical element 132 as shown in FIG. 1. Preferably but not exclusively, the light source 131' has a long-coherence-length property. Consequently, the plural light beams of the polarized light L2 and the plural light beams of the external lights L3 still have the interference effects after propagation. In other words, the reactions or responses according to the inherent information of the under-test object 9 can be effectively classified. Consequently, the efficacy of recognizing the spectrum is enhanced.

In this embodiment, the optical device 1C further comprises a first lens unit 151 and a second lens unit 152. The first lens unit 151 is arranged between the polarized light generation unit 13' and the under-test object 9. After the polarized light L2 from the polarized light generation unit 13' is collimated or focused by the first lens unit 151, the collimated or focused polarized light L2 is projected on the under-test object 9. The second lens unit 152 is arranged between the under-test object 9 and the spectrum response analysis unit 14. After the at least a portion of the scattered light from the under-test object 9 (i.e., the external light L3) is collimated or focused by the second lens unit 152, the collimated or focused polarized external light L3 is transmitted to the spectrum response analysis unit 14.

Figure 4:
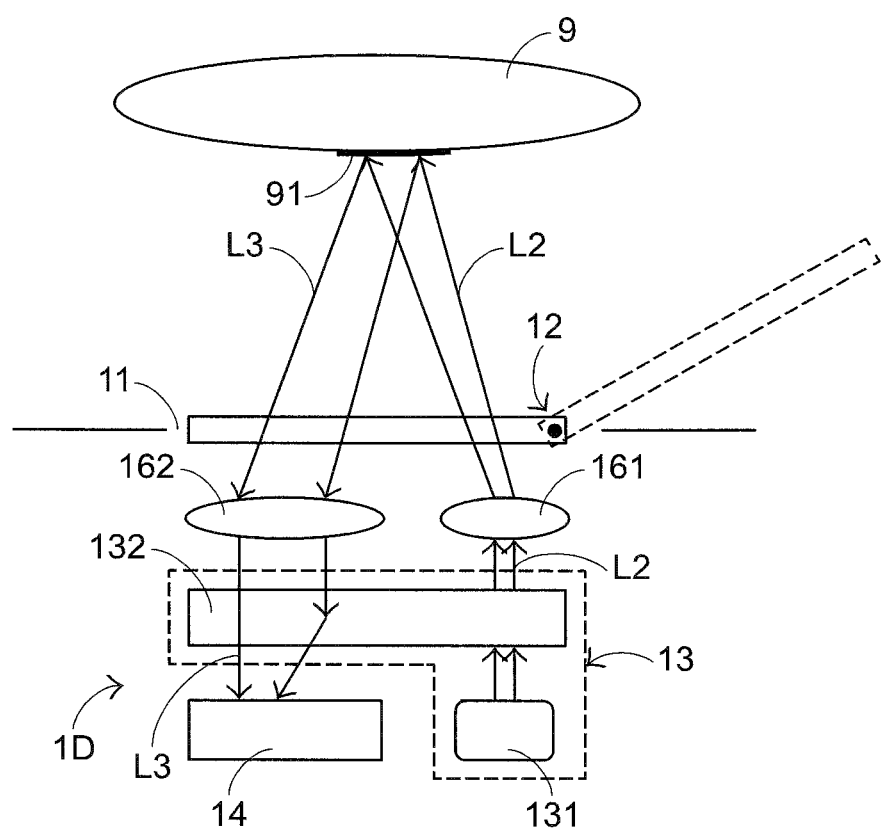
FIG. 4 schematically illustrates the operating concept of an optical device according to a fourth embodiment of the present invention.

FIG. 4 schematically illustrates the operating concept of an optical device according to a fourth embodiment of the present invention. The structure and function of the optical device 1D that are similar to those of the first embodiment are not redundantly described herein. In comparison with the first embodiment, the optical device 1D of this embodiment further comprises a first lens unit 161 and a second lens unit 162. The first lens unit 161 is arranged between the polarized light generation unit 13 and the under-test object 9. After the polarized light L2 from the polarized light generation unit 13' passes through the first lens unit 161, a size and/or a position of a projected area 91 of the polarized light L2 on the under-test object 9 is adjusted. The second lens unit 162 is arranged between the under-test object 9 and the spectrum response analysis unit 14 in order to collect the at least a portion of the scattered light from the under-test object 9 (i.e., the external light L3).

The light-receiving capability of the second lens unit 162 is determined according to the size and/or the position of the projected area 91 on the under-test object 9. In other words, the light-receiving capability of the second lens unit 162 can be enhanced by using the first lens unit 161 to adjust the size and/or the position of the projected area 91 on the under-test object 9. Since the light-receiving capability of the second lens unit 162 is enhanced, more light beams of the scattered light from the under-test object 9 (i.e., the external light L3) can be returned back to the spectrum response analysis unit 14 of the optical device 1D. Under this circumstance, the accuracy of the spectrum response analysis result of the spectrum response analysis unit 14 is enhanced.

Figure 5:
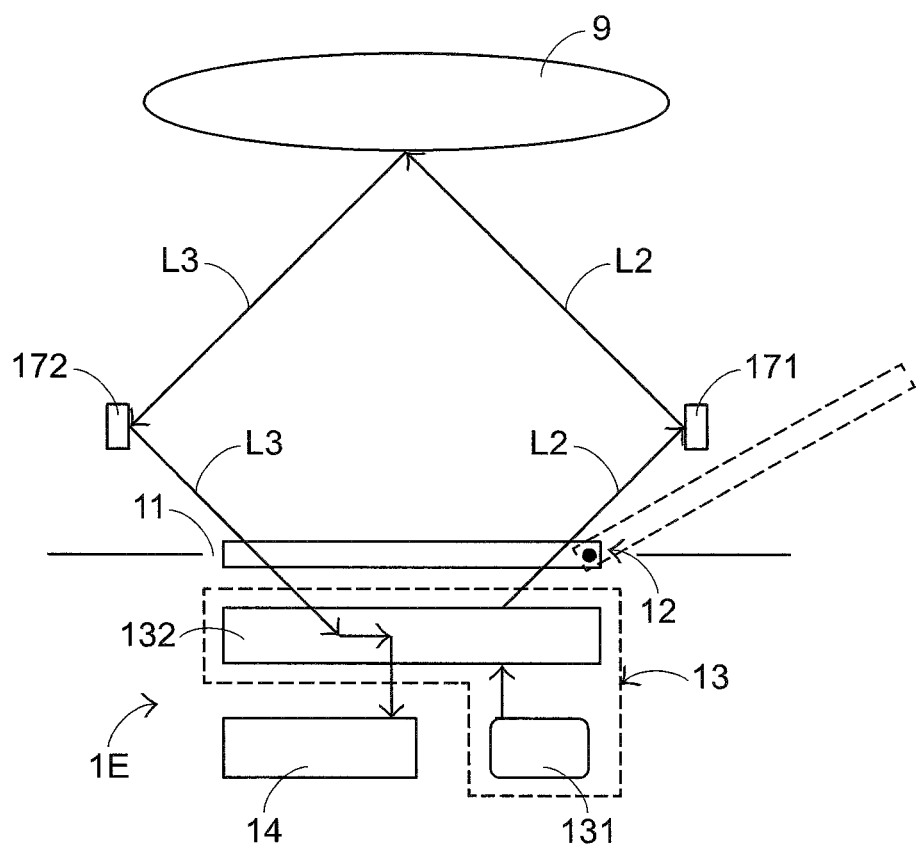
FIG. 5 schematically illustrates the operating concept of an optical device according to a fifth embodiment of the present invention.

FIG. 5 schematically illustrates the operating concept of an optical device according to a fifth embodiment of the present invention. The structure and function of the optical device 1E that are similar to those of the first embodiment are not redundantly described herein. In comparison with the first embodiment, the optical device 1E of this embodiment further comprises a first reflective optical unit 171 and a second reflective optical unit 172 according to the optical path requirement. The first reflective optical unit 171 is arranged between the polarized light generation unit 13 and the under-test object 9. The traveling direction of the polarized light L2 from the polarized light generation unit 13 is guided by the first reflective optical unit 171. Consequently, the polarized light L2 is projected on the under-test object 9. The second reflective optical unit 172 is arranged between the under-test object 9 and the spectrum response analysis unit 14. The traveling direction of the at least a portion of the scattered light from the under-test object 9 (i.e., the external light L3) is guided by the second reflective optical unit 172. Consequently, the external light L3 is returned back and transmitted to the spectrum response analysis unit 14 of the optical device 1E.

FIG. 6 schematically illustrates a portable electronic product using the optical device of the present invention. An example of the portable electronic product 2 includes but is not limited to a mobile phone, a tablet computer or a wearable device. The portable electronic product 2 is equipped with the optical device 1. The optical device 1 is the optical device of any of the above embodiments. When the portable electronic product 2 is carried by the user, the optical device 1 can be used to obtain the inherent information of any under-test object 9. For example, the inherent information includes the air quality, the food calorie, the fruit sweetness or the plant growth condition. Especially, since people pay much attention to food safety in recent years, the industrial value of the optical device of the present invention is more obvious. For example, the optical device of the present invention can be used to detect the ingredients of food before the user eats the food. The optical device as shown in FIG. 6 is presented herein for purpose of illustration and description only. It is noted that the optical device 6 of the present invention may be applied to other electronic products while retaining the teachings of the invention.

From the above descriptions, the present invention provides an optical device with enhanced signal-to-noise ratio (S/N ratio) and reduced overall thickness. During the process of detecting the under-test object, the pattern of the light projected on the under-test object is more diverse. For example, the light projected on the under-test object includes one of a linearly polarized light (e.g., an S-polarized light or a P-polarized light), a circularly polarized light and an elliptically polarized light. When a different pattern of the light is projected on the under-test object, a different spectrum response is produced. After the spectrum response analysis is completed, the optical device is capable of acquiring more explicit and diverse inherent information of the under-test object.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. An optical device, comprising:
   at least one door;
   a polarized light generation unit located at a first side of the at least one door, and generating at least one polarized light;
   a spectrum response analysis unit located at the first side of the at least one door; and
   a door control unit for opening or closing the at least one door,
   wherein when the at least one door is opened by the door control unit, the at least one polarized light is transmitted through the at least one door and externally projected on an under-test object at a second side of the at least one door, so that a scattered light is generated, wherein after at least a portion of the scattered light from the under-test object is returned back and transmitted through the at least one door, the at least a portion of the scattered light is projected on the spectrum response analysis unit, so that the spectrum response analysis unit performs a spectrum response analysis on the at least a portion of the scattered light, wherein the door is selectively opened or closed by the door control unit according to a time-sequence programming.

2. The optical device according to claim 1, wherein the at least one polarized light includes at least one of a linearly polarized light, a circularly polarized light and an elliptically polarized light.

3. The optical device according to claim 1, wherein the polarized light generation unit comprises a light source.

4. The optical device according to claim 3, wherein the light source is a polarized light source.

5. The optical device according to claim 4, wherein the light source has a long-coherence-length property.

6. The optical device according to claim 3, wherein the light source includes at least one of a laser diode, a light emitting diode, an organic light emitting diode and a thermal source.

7. The optical device according to claim 3, wherein the polarized light generation unit further comprises an optical element, and the optical element is arranged between the at least one door and the light source, wherein when a source light from the light source is introduced into the optical element, the source light is split into the at least one polarized light by the optical element.

8. The optical device according to claim 7, wherein after the at least a portion of the scattered light from the under-test object is returned back and transmitted through the at least one door, the at least a portion of the scattered light is guided to the spectrum response analysis unit by the optical element.

9. The optical device according to claim 7, wherein the optical element includes a diffractive optical element.

10. The optical device according to claim 9, wherein the diffractive optical element is a diffractive optical film.

11. The optical device according to claim 7, wherein at least one of a wavelength-dependent coating and a polarization-dependent coating is formed on the optical element.

12. The optical device according to claim 1, wherein the at least one door is a single door that is shared by the polarized light generation unit and the spectrum response analysis unit, or the at least one door comprises a first door corresponding to the polarized light generation unit and a second door corresponding to the spectrum response analysis unit.

13. The optical device according to claim 12, wherein the first door and the second door are simultaneously opened or simultaneously closed.

14. The optical device according to claim 1, wherein after the spectrum response analysis is performed, an inherent information of the under-test object is obtained.

15. The optical device according to claim 14, wherein the inherent information contains an ingredient information, a material information, a texture information or a property information.

16. The optical device according to claim 1, wherein the optical device is included in a portable electronic product.

17. The optical device according to claim 1, wherein a thickness of the optical device is not larger than 7 mm.

18. The optical device according to claim 1, wherein the optical device further comprises a lens unit, wherein the lens unit is arranged between the polarized light generation unit and the under-test object for collimating or focusing the at least one polarized light from the polarized light generation unit to the under-test object, or the lens unit is arranged between the under-test object and the spectrum response analysis unit for collimating or focusing the at least a portion of the scattered light from the under-test object to the spectrum response analysis unit.

19. The optical device according to claim 1, wherein the optical device further comprises a reflective optical unit, wherein the reflective optical unit is arranged between the polarized light generation unit and the under-test object for guiding a traveling direction of the at least one polarized light from the polarized light generation unit, or the reflective optical unit is arranged between the under-test object and the spectrum response analysis unit for guiding a traveling direction of the at least a portion of the scattered light from the under-test object.

20. The optical device according to claim 1, wherein the optical device further comprises a first lens unit and a second lens unit, wherein the first lens unit is arranged between the polarized light generation unit and the under-test object, and the second lens unit is arranged between the under-test object and the spectrum response analysis unit, wherein the at least a portion of the scattered light is collected by the second lens unit, wherein after the at least one polarized light from the polarized light generation unit passes through the first lens unit, a projected area of the at least one polarized light on the under-test object is adjusted.

21. The optical device according to claim 1, wherein the polarized light generation unit is controlled by a time-varying programming such that a degree of polarization and intensity is varied.

22. The optical device according to claim 1, wherein the at least one polarized light comprises a polarized structured light pattern with polarized property which is further detected by the spectrum response analysis unit which is a two-dimensional detection unit.

23. The optical device according to claim 22, wherein the polarized structured light pattern is varied with time which is programming by controlling the polarized light generation unit or the door control unit.

\* \* \* \* \*